United States Patent [19]

Sugita et al.

[11] Patent Number: 4,969,890
[45] Date of Patent: Nov. 13, 1990

[54] CATHETER

[75] Inventors: Yoichi Sugita, Tokyo; Takashi Kawabata, Hasuda, both of Japan

[73] Assignee: Nippon Zeon Co., Ltd., Tokyo, Japan

[21] Appl. No.: 217,483

[22] Filed: Jul. 7, 1988

[30] Foreign Application Priority Data

Jul. 10, 1987 [JP] Japan .................................. 62-173643

[51] Int. Cl.⁵ ............................................ A61M 29/00
[52] U.S. Cl. .......................................... 606/192; 623/1
[58] Field of Search .................... 128/341–344, 128/348.1, 745, 394 R; 604/101, 8, 272–274, 96; 623/1, 11–13, 66; 606/191–194, 200

[56] References Cited

U.S. PATENT DOCUMENTS

| 4,299,226 | 11/1981 | Banka ................................ 128/344 |
| 4,503,569 | 3/1985 | Dotter ............................... 128/343 |
| 4,740,207 | 4/1986 | Kreamer .......................... 128/343 |
| 4,776,337 | 10/1988 | Palmaz ............................ 128/343 |
| 4,795,458 | 1/1989 | Regan .................................. 623/1 |

FOREIGN PATENT DOCUMENTS 0654214  2/1986  Switzerland ..................... 604/101

Primary Examiner—C. Fred Rosenbaum
Assistant Examiner—William W. Lewis
Attorney, Agent, or Firm—Armstrong, Nikaido, Marmelstein, Kubovcik & Murray

[57] ABSTRACT

There is provided a catheter composed of a main body fitted with a shape memory alloy member and having a liquid injection means to supply warming liquid to have said member recover the original shape thereof.

9 Claims, 10 Drawing Sheets (A) (B) (C)

(A)

(B)

(C)

(D)

(A)

(B)

(A) (B)

(A)

(B)

(A)

(B)

(C)

(D)

(E)

CATHETER

BACKGROUND OF THE INVENTION

1. Field of the Invention

This invention relates to a catheter and more specifically one for use to permanently dilate the stenosis of a tubular organ such as blood vessel.

2. Description of the Prior Art

For treatment of angina pectoris or cardiac infarction, the so-called PTCA (Percutaneous Transluminal Coronary Angioplasty) catheter has hitherto been inserted, for example, into the stenosis of coronary artery of patient depending on cases. Namely, for treatment of a the disease caused by stenosis of the coronary artery, besides the chemical treatment making use of a thrombolytic agent or the like, a surgical treatment is available to expand the stenosis with the PTCA catheter.

This kind of catheter has a rubber balloon at the leading end thereof. As the catheter is inserted into the blood vessel to reach the stenosis thereof, the balloon is inflated to expand against the vessel wall of stenosis. The catheter is then withdrawn. Though rather easy to perform, the above surgical treatment has a disadvantage that the effect of the treatment is not permanent, so the restenosis rate is high.

As an approach to improve the above defect, a system is proposed which places a endoprosthesis made of a shape memory alloy in the blood vessel (the endoprosthesis is then covered with tissues). For example, there are two patents, U.S. Pat. No. 3,868,956 and Japanese Patent Publication No. 61-6655. The former discloses a method wherein a shape memory alloy is worked as a endoprosthesis, its memory is by heating the wire memory of the original shape and deformed to a shape of a narrower diameter, which is fitted by use of a catheter into the stenosis of a blood vessel and then heated by use of electrical energy to restore the original shape and thereby dilate the blood vessel to expand the stenosis thereof. The latter patent discloses a method wherein a piece of shape memory alloy sheet, which is worked to a endoprosthesis of a diameter equivalent to the inner diameter of normal blood vessel without stenosis, annealed and deformed to a narrower diameter, is fitted into a desirable position of blood vessel with the use of a catheter and then heated by use of a laser beam or high frequency induction to restore the original shape thereof.

With the former approach, however, the deformed endoprosthesis of shape memory alloy is electrically heated by use of either an additional heater or the electrical resistance of the shape memory alloy itself, so there is a danger of current leak that might give an electric shock and yet it is necessary to use a complex system. Instead of an electrical current as used by the former approach, the latter approach uses laser beam or high frequency induction for heating, which will require an expensive complex system, though not mentioned in that invention.

OBJECTS AND SUMMARY OF THE INVENTION

It is an object of the invention to provide a catheter that can be used for satisfactory permanent treatment (particularly dilation) of the stenosis of a blood vessel or the like without any later restenosis.

It is another object of the invention to provide a catheter that allows quick injection of warming solution or the like and itself can be worked to a narrower diameter for improved manipulatability.

Namely, the invention relates to a catheter comprising a main body fitted with a shape memory alloy member and having a liquid injection means to supply liquid for shape change of the shape memory alloy member.

Other objects, features and advantages of the invention will appear more fully from the following detailed description thereof taken in connection with the accompanying drawings.

DESCRIPTION OF THE PREFERRED EMBODIMENTS

Figure 1:
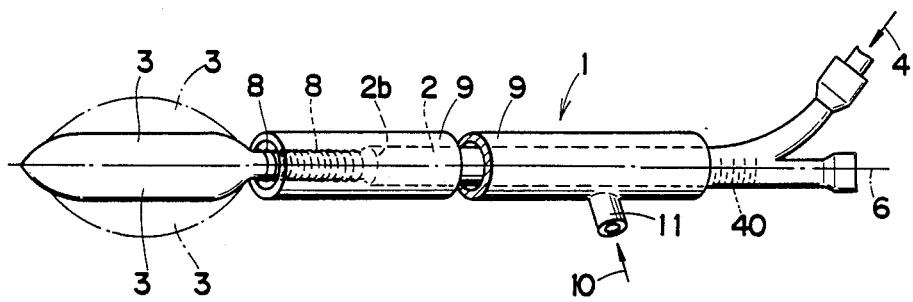
FIG. 1 is a perspective view of a catheter of the invention.
Figure 2:
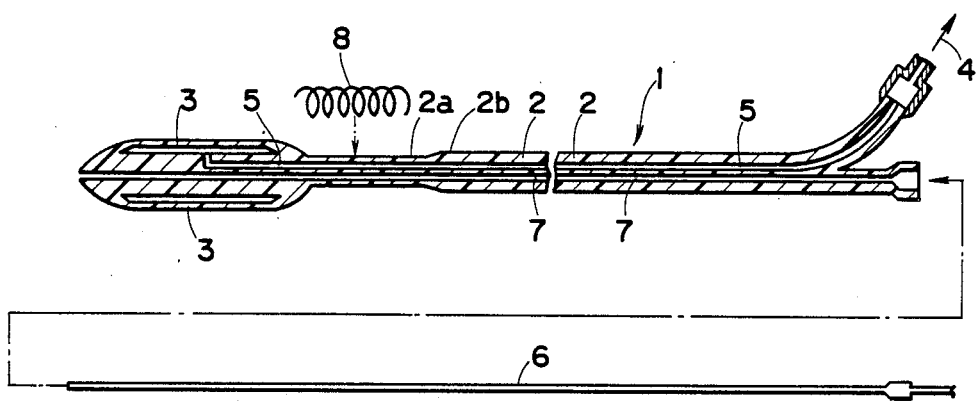
FIG. 2 is a longitudinal section of the main part of the catheter of FIG. 1 without sheath.
Figure 3:
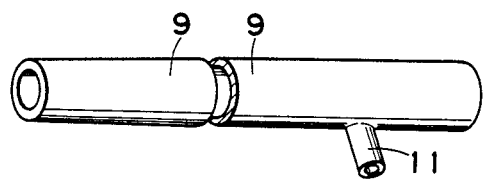
FIG. 3 is a perspective view of the sheath of FIG. 1.
Figure 4:
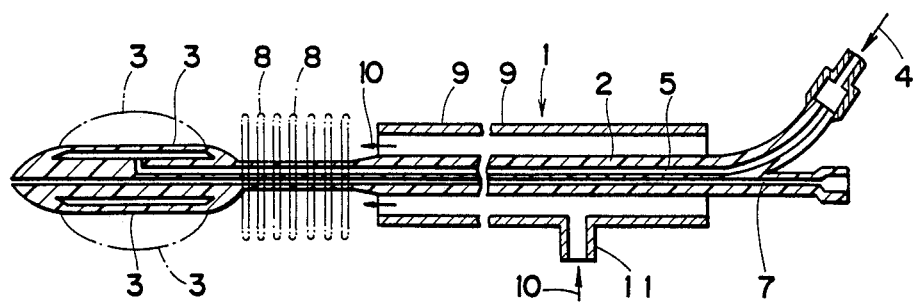
FIG. 4 is a longitudinal section of the catheter of FIG. 1 showing the recovery of the original shape of a shape memory alloy coil thereon.

FIGS. 1 through 4 give an example of the catheter of the invention.

In this case a PTCA catheter 1 comprises a main body 2 made of polyethylene, polyvinyl chloride, silicone rubber, polyurethane elastomer or the like and a balloon 3 made of elastic rubber attached to the tapering end of main body 2 and has a lumen 5 in the main body 2 along the length thereof to inject physiological saline 4, contrast medium or their mixture in the balloon 3 (or drain the same). Along the axis of the main body 2, a throughhole lumen 7 to pass a guide wire 6 through is formed from end to end. A little behind the balloon 3, a shape memory alloy coil 8 made of a shape memory alloy) for example, Ni-Ti alloy, is attached. Further, except for the part of main body 2 fitted with the balloon 3, almost the full length of the main body 2 is covered with a sheath 9, for example, made of polyurethane elastomer. The sheath 9 branches near the trailing end thereof to provide an inlet port 11 to inject warming liquid 10.

In the above setup, the coil 8 has such a property as to restore the original shape, namely, expand at a temperature above the transition point (transformation point Af) of the shape memory alloy. Being used in a human body, the coil 8 is preferably made of a shape memory alloy whose transition temperature is at least 3° C. higher than the body temperature and particularly between 38 and 48° C. Such transition temperature can be achieved by selecting a proper composition of the shape memory alloy. From the inlet port 11 of sheath 9, warming liquid 10 is injected to flow through a space as defined by the inside surface of sheath 9 and outside surface of main body 2 to reach the coil 8. For the above heating liquid, a transfusion solution, physiological saline, contrast medium etc. may be used, which is warmed hot enough in full consideration of a fact that the temperature lowers as the solution flows out of the catheter and mixes with blood or body fluid but not so hot as to cause any heating damage of the innerwall in the blood vessel.

For the above coil 8, a wire of shape memory alloy is wound to a coil of a desired diameter, annealed and then rewound to a coil of a smaller diameter around the outside of main body 2. To avoid the coil from sliding from the given position, the corresponding part 2a of main body is narrowed to a smaller outer diameter. It is a matter of course that instead of narrowing that part the coil may be stopped with a retaining ring, for example, made of silicone rubber or the like.

Figure 6:
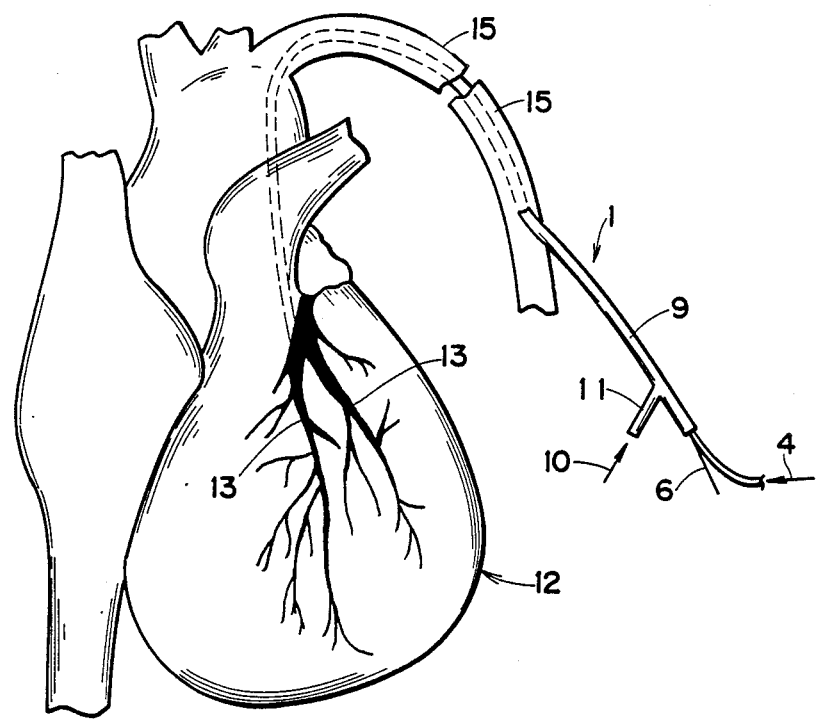
FIG. 6 is a sketch of the path along which the catheter is inserted into the coronary artery of heart.

As in FIG. 6, the catheter 1 of the above setup is inserted with the balloon fitted at the tapering end, for example, from a femoral artery 15 as far as the coronary artery 13 of the patient's heart 12 (it is noted that only a schematic sketch is given to ease the understanding). The main catheter 2 is guided to the given position by the sheath 9, when the guide wire 6 as mentioned above is available for satisfactory control. The catheter, as it is guided, can be monitored by roentogenography of the catheter and shape memory alloy coil.

Figure 5:
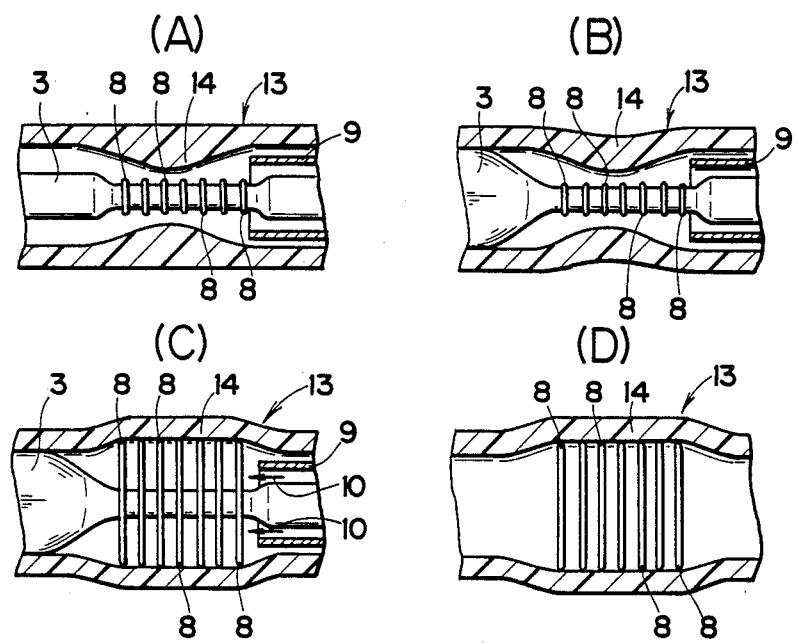
FIGS. 5 (A), (B), (C) and (D) are enlarged sections of a stenosis of blood vessel fitted with the essential part of the catheter of FIG. 1 and correspond to successive steps of the treatment of the stenosis.

After the catheter is successfully inserted to a stenosis 14 of artery 13 as in FIG. 5 (A), physiological saline or the like 4 is injected to inflate the balloon 3 so the balloon 3 may come in close contact to the inner wall of blood vessel as in FIG. 5 (B) temporarily stopping the flow of blood and other body fluid there. It is noted that the main body 2 must be moved ahead beforehand by the control of guide wire 6 so far as the coil 8 is uncovered from the sheath 9 for exposure as in FIG. 5 (A). In FIG. 5 (C), physiological saline 10 warmed, for example, to a constant temperature of 50° C. is injected from the inlet port 11 of the sheath 9. The warmed physiological saline 10 from the inlet port 11 flows, as indicated clearly in FIG. 4, along a space formed inside the sheath 9 (and outside of the main body) to pour where the coil 8 is located. Physiological saline, as it comes out of the sheath and mixes with blood and other body fluid that remain there, becomes cooler at first but the temperature rises gradually until the coil 8 is warmed hotter than the transition temperature thereof to recover the original expanded shape as indicated by solid lines in FIG. 5 (C) or interrupted lines in FIG. 4. The balloon 3 is then deflated by letting physiological saline out and the catheter is pulled out as in FIG. 5 (D). The stenosis 14 thus remains expanded with the coil 8 left therein to achieve the intended object of the treatment. It is noted that graduations 40 are preferably added as indicated by interrupted lines in FIG. 1 to give a measure of the distance by which the main body is moved relative to the sheath 9 as mentioned above and further that at the back of coil 8 a bulge (or projection) 2b is provided to stop the coil 8.

With the catheter 1 of the above example, the stenosis of a blood vessel can be expanded permanently, as mentioned above, without any danger of restenosis. Further, since the warming liquid is not passed through inside of the main body but outside thereof and inside of the sheath, a larger lumen can be secured for the liquid flow, allowing use of a warming liquid of lower temperature. This means safer operation, faster liquid injection, and also that the main body itself can be made thinner (since the lumen for the passage of warming liquid is not necessary). As a result, this kind of catheter is easy to insert into a fine vessel such as the coronary artery. Further, with use of the sheath, the catheter can be inserted easier and more reliably.

Different from the heating methods of prior art, the shape memory alloy coil 8 is heated with warmed physiological saline or transfusion solution which can be injected under full temperature control. Thus, the surgery is much safer. In addition, it is easy to prepare warming liquid of a given temperature. This means a reducing of surgery cost.

The above catheter can be percutaneously inserted from the femoral artery or other blood vessels, being particularly useful for the therapy of angina pectoris and acute myocardial infarction.

Figure 7:
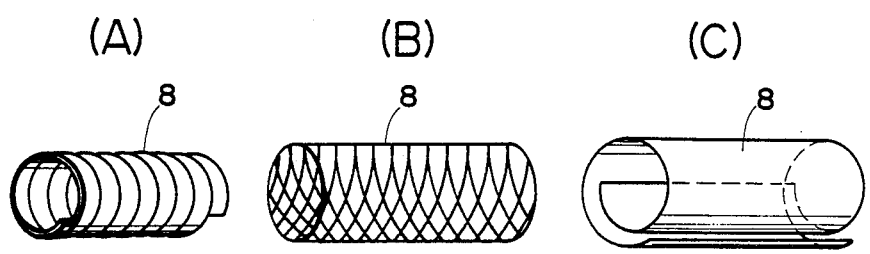
FIGS. 7 (A), (B) and (C) are perspective views of other tissues dilaters.

Though a wire coil 8 of shape memory alloy is applied in the above example, a spring sheet coil or a coil of oval cross-section of FIG. 7 (A) having a ratio of the major transversal axis length to the minor conjugate axis length in the range of 1.0 to 20, preferably 1.5 to 10, more preferably 2.0 to 5.0, woven tube or meshwork of FIG. 7 (B), rolled sheet of FIG. 7 (C), or a endoprosthesis of expandable metal etc. not shown can be used instead.

Figure 9:
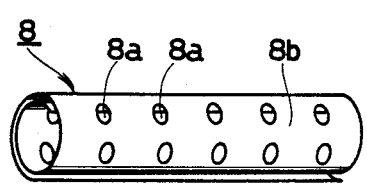
FIGS. 9 (A) and (B) are perspective views of another design of the tubular piece of shape memory alloy of the invention, corresponding to the deformed shape and original shape, respectively.
Figure 9:
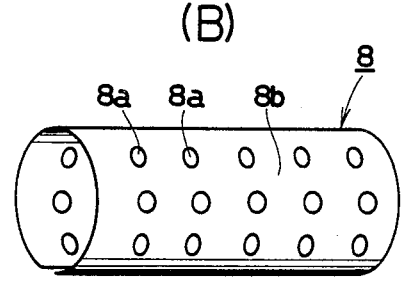
Figure 10:
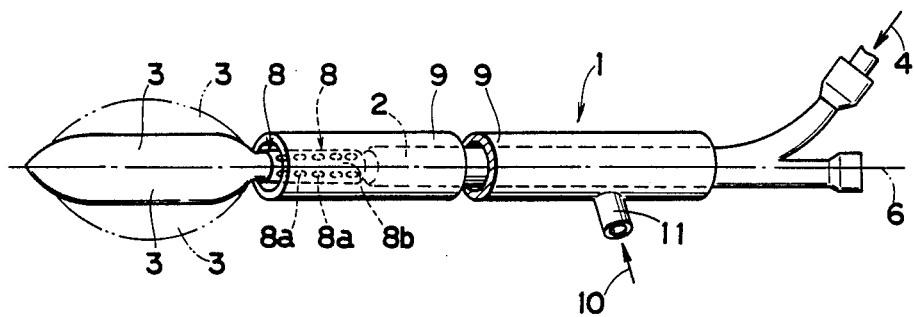
FIG. 10 is a perspective view of another example of the catheter of the invention.
Figure 11:
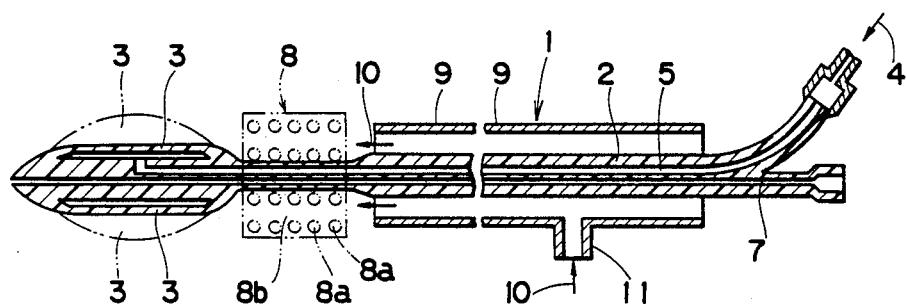
FIG. 11 is a longitudinal section of the catheter of FIG. 10 showing the recovery of the original shape of a shape memory alloy coil thereon.

FIGS. 9 through 12 give another example of the catheter of the invention. Slightly behind a balloon 3, a shape memory alloy tubular piece 8 is put, which is a roll of Ni-Ti sheet formed with many through-holes 8a. For the above tubular piece 8, a sheet of shape memory alloy 8, for example, Ni-Ti alloy (with 50 atomic percent Ni) formed with many throughholes 8a is wound to a roll as shown in FIG. 9 (B), annealed 20 to 40 min at 400 to 500° C. for memory of the original shape, and then rewound to a roll of smaller diameter as in FIG. 9 (A).

Figure 12:
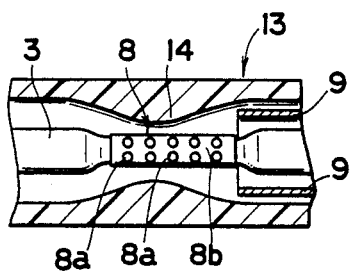
FIGS. 12 (A), (B), (C) and (D) are enlarged longitudinal sections of a stenosis of blood vessel fitted with the essential part of the catheter of FIG. 10 and correspond to successive steps of the patency of a stenosis.
Figure 12:
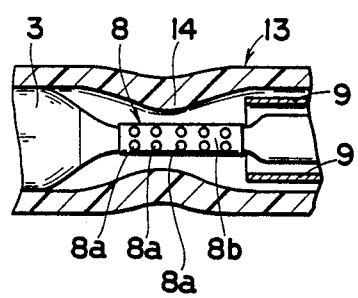
Figure 12:
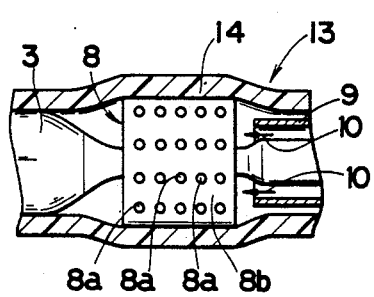
Figure 12:
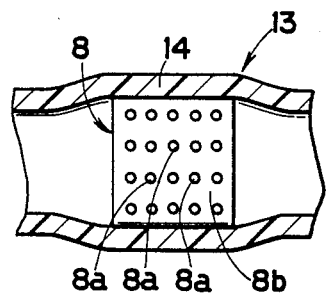

As shown in FIG. 12 (A), the catheter is inserted as far as the stenosis 14 of blood vessel 13 and, as shown in FIG. 12 (B), a solution, for example, physiological saline 4 is injected to inflate the balloon 3 so the balloon may come in close contact to the inner wall of blood vessel, stopping the flow of blood and other body fluid temporarily. As shown in FIG. 12 (C), physiological saline 10, for example, warned to a constant temperature of 50° C. is injected from the inlet port 11 on the sheath 9. Warmed physiological saline 10 heats the tubular piece 8 hotter than the transition point, so the piece 8 unwinds to the original shape (solid lines in FIG. 12 (C) and interrupted lines in FIG. 11). At this state, therefore, the tubular piece has unwound to the original shape as shown in FIG. 9 (B). When the tubular piece 8 changes shape from FIG. 9 (A) to FIG. 9 (B), the length of the longitudinal dimension thereof has no substantial change because the shape memory alloy member, namely, tubular piece 8 is not coiled but has longitudinally continuous regions 8b. Accordingly, there is no danger that the coil 8 may partially (or fully) slide off the stenosis 14. As a result, the endoprosthesis 8 can expand easily and securely the whole length of stenosis 14 as shown in FIGS. 12 (C) and (D).

In addition to the merits as mentioned above, the above example of catheter has such a merit that the inside surface of blood vessel 13 is left uncovered at many throughholes 8a of tubular piece 8 allowing formation of endothelial tissues there. This gives an effect that the endoprosthesis 8 is ultimately embedded in tissues of blood vessel 13 to maintain the dilation of the stenosis continuously and hygienically for a prolonged period of time.

In the tubular piece 8, there are many longitudinal alignments of throughholes 8a, with longitudinally continuous regions 8b left therebetween. Such continuous regions are just intended to substantially prevent the dimensional change of endoprosthesis 8 in the longitudinal direction after shape change. Therefore, throughholes may be opened in zigzag arrays to leave a substantially continuous region (meandering continuous region) in the longitudinal direction.

Figure 13:
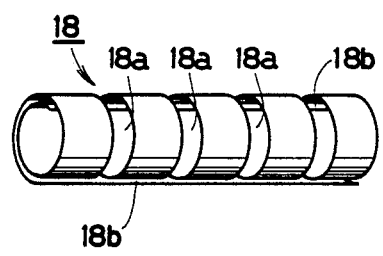
FIGS. 13 (A) and (B) are perspective views of another design of the endoprosthesis of shape memory alloy of the invention, corresponding to the deformed shape and original shape, respectively.
Figure 13:
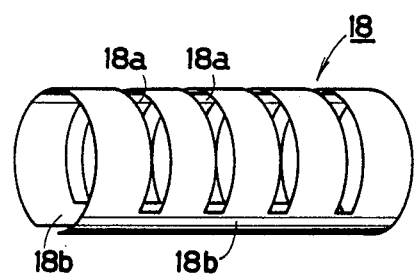
Figure 14:
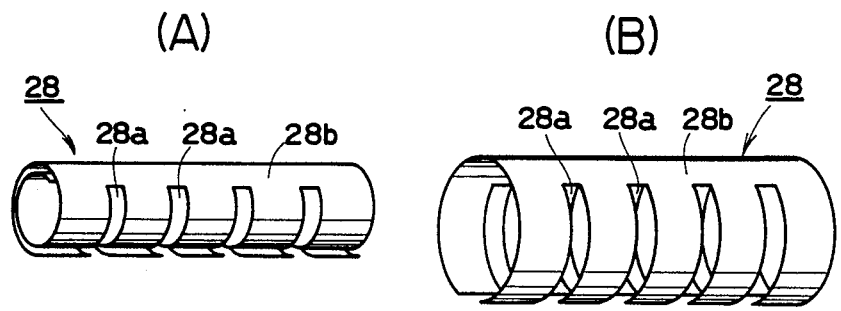
FIGS. 14 (A) and (B) are perspective views of another design of the endoprosthesis of shape memory alloy of the invention, corresponding to the deformed shape and original shape, respectively.

Besides, as in FIGS. 13 (A) and (B), a shape memory alloy endoprosthesis 18 may be used which has a number of slits 18a cut in the circumferential direction with both margins left to provide the longitudinally continuous region 18b. Or as in FIGS. 14 (A) and (B), a shape memory alloy endoprosthesis 28 may be used which has a number of slits 28a cut in the circumferential direction in a rib-like configuration with the central region left intact to provide the longitudinally continuous region 28b. Both in FIGS. 13 and 14, the sketches (A) and (B) correspond to the deformed shape and original shape, respectively.

FIGS. 15 through 20 give another example of the catheter of the invention. A remarkable feature of this example is that the middle region 8c of the coil 8 has a transition point lower than at both end regions 8d thereof. A detailed description will be given about this point below.

Figure 15:
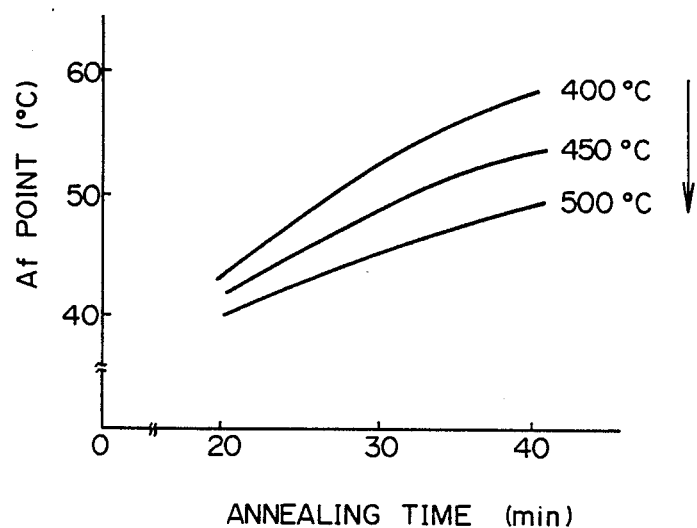
FIG. 15 is a diagram showing the relation between the heat treatment condition and transition temperature of a shape memory alloy.

Even a same composition of shape memory alloy may have a different transition point depending on the condition of annealing process for memorizing the original shape. FIG. 15 shows three curves of annealing time versus transition point Af, corresponding to heating temperatures of 400, 450 and 500° C., respectively.

Figure 16:
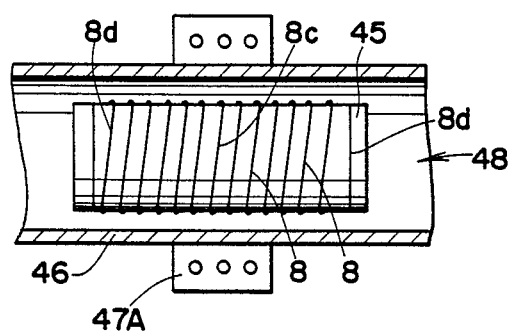
FIG. 16 is a schematic section of a heating furnace.

To give the aforementioned distribution of transition point along the coil 8, a setup of FIG. 16 is used. A shape memory alloy wire 8 is wound around a cylindrical metal mold 45 at given pitches and put into a furnace core tube 46. In a stream of inert gas 48, the coil 8 is then heated by a heater 47A located around the middle region of coil 8. The middle region 8c of coil 8, which is closer to the heater 47A, is heated hottest and in both end regions 8d of coil 8 the farther from the heater 47A, the lower the heating temperature. A coil thus worked to the dimensions of metal mold 45 and annealed for memory of the original shape is wound around the given part of catheter having a smaller diameter to give a coil of the corresponding diameter. Alternatively, after the coil is annealed at a uniform temperature for memory of the original shape, both end regions of the coil may be coated with a thermal insulator material. Also when the latter type of coil is applied, the middle part of coil reaches the transition temperature earlier than the both end regions thereof.

For each of the above two types of coil, an example will be given below.

(1) For the former type, Ni-Ti alloy of 0.5 mm in diameter wire (50 atomic percent Ni) was wound around a metal mold to form a coil 5 mm in diameter, which was annealed 30 min using a setup of FIG. 16. For annealing, the middle region 8c was heated at 500° C. and both end regions 8d at 450° C. The wire of the coil was wound around the catheter to give a coil 2.5 mm in diameter.

(2) For the latter type, a Ni-Ti alloy wire wound around a metal mold by the same method as in the above example (1) was heated 30 min at a uniform temperature of 500° C. The coil was then coated with polyurethane solution as far as 1.5 mm from both ends. After drying, there was formed 0.05 mm thick polyurethane coating. The wire of the above coil was rewound to a coil of smaller diameter as in the above example (1).

Figure 17:
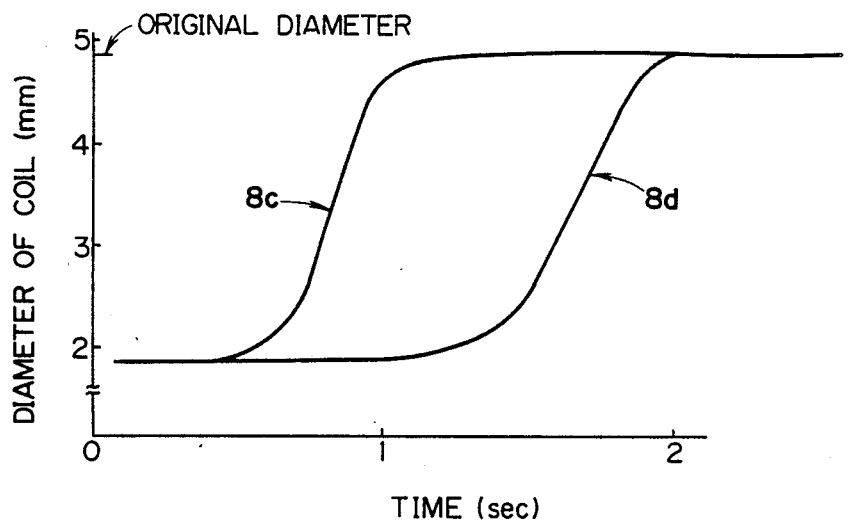
FIGS. 17 (A) and (B) refer to another two examples of the shape memory alloy coil of the invention, each showing the time course of the recovery of the original shape at different parts of the shape memory alloy coil.
Figure 17:
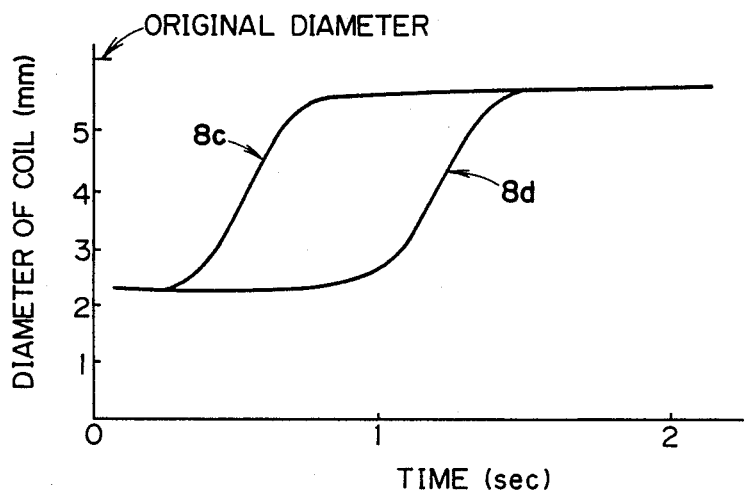

The coils thus made were each immersed in running water of 45° C. to determine how the original shape was restored with time. FIGS. 17 (A) and (B), referring to the above coil examples (1) and (2), respectively, give a rough idea about the restoration of the original shape with these examples.

It is seen from FIGS. 17 (A) and (B) that with both coil examples, the middle region 8c of the coil started recovery of the original shape in the running warm water earlier than the end regions 8d. In case of the coil example (1), the middle region 8c is annealed at higher temperatures than both end regions 8d, so the middle region 8c has lower transition points as compared to the both end regions 8d (see FIG. 15). After the start of warm water passage, therefore, first, the middle region 8c reaches the transition points thereof to restore the original shape and both end regions 8d do so with a delay. In case of the coil example (2), because of polyurethane coating, both end regions 8d warm slower than the middle region 8c, so the regions 8d reach the transition point later than the region 8c.

Figure 18:
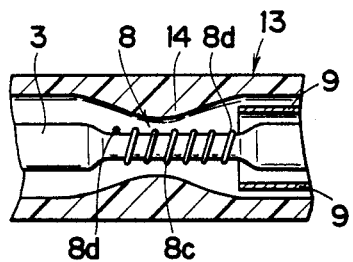
FIGS. 18 (A), (B), (C), (D) and (E) are enlarged sections of a stenosis of blood vessel fitted with the essential part of another example of the catheter of the invention and correspond to successive steps of the patency of stenosis.
Figure 18:
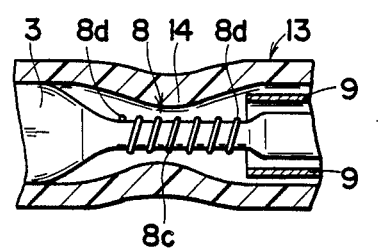
Figure 18:
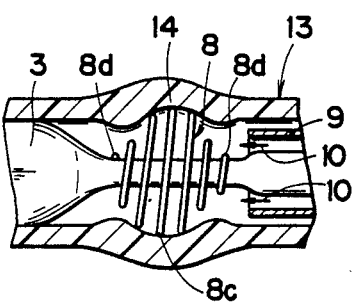
Figure 18:
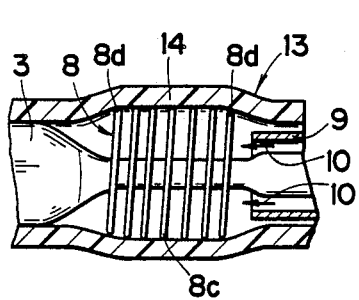
Figure 18:
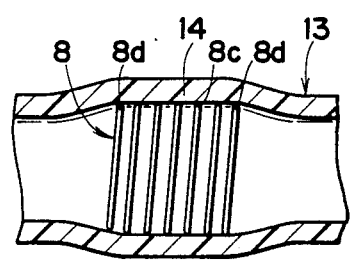

As the catheter is inserted as far as the stenosis 14 of blood vessel 13 as shown in FIG. 18 (A), physiological saline or the like 4 is injected to inflate the balloon 3 as in FIG. 18 (B). The balloon 3 is thus brought in close contact to the inside wall of blood vessel to temporarily stop the blood flow and other body fluid. Dilation of the stenosis 14 is then started as in FIG. 18 (C). As the recovery of the original shape of the coil extends toward both ends, the whole length of stenosis 14 is dilated as in FIG. 18 (D). Finally, the balloon 3 is deflated and the catheter is withdrawn as in FIG. 18 (E).

According to the above example, the coil 8 starts expanding first at the middle region thereof at the step of FIG. 18 (C). Expanding extends toward both ends and finally the both end regions 8d stretch. Thus, the coil can expand and recover the original shape thereof without any constraint, resulting in reliable dilation of the whole length of stenosis 14. Namely, since at least the end regions of the coil differ from the middle region thereof in the transformation start condition of shape memory alloy (for example, the transformation start temperature and/or timing), the shape memory alloy coil can change the shape thereof in a more desirable mode (for example, individual regions of the coil changing shape in proper time sequence). As a result, the shape memory alloy coil can rewind the original shape smoothly along the whole length thereof with no such trouble that the recovery of the original shape at one region of coil may prevent or suppress the recovery of the original shape at any other region thereof. Accordingly, the affected part of a patient's body, for example, a blood vessel can reliably be treated. Further, if such shape memory alloy coil is retained at the treated part of a patient's body, recurrence of the trouble (for example, restenosis of blood vessel) can reliably be prevented there.

To endow the coil with a distribution of transition point as mentioned with the above coil example (1), the following methods are available besides the one as described above referring to FIG. 16.

Figure 19:
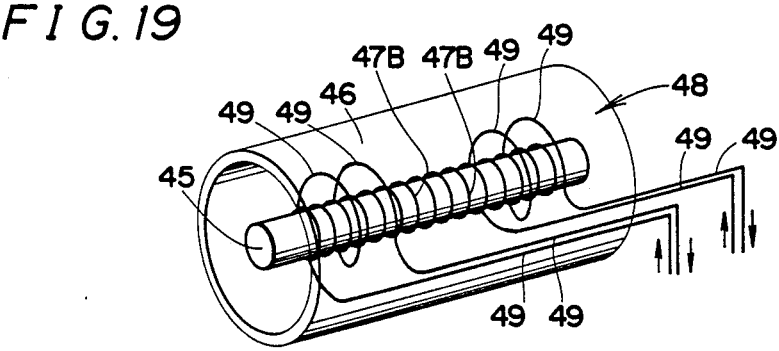
FIGS. 19 and 20 are schematic perspective inside views of other examples of the heating furnaces used for the invention.

In FIG. 19, a coil heater 47B is installed inside a furnace core tube 46. A Ni-Ti alloy wire coil (not shown) wound around a metal mold 45 is inserted inside the heater 47B and a cooling line 49 (coiled pipe for cooling liquid circulation) is added around each end of the wire coil. Thus, individual regions of the wire coil can be annealed at different temperatures as with the coil example (1) to achieve the intended distribution of transition point along the length of coil.

Figure 20:
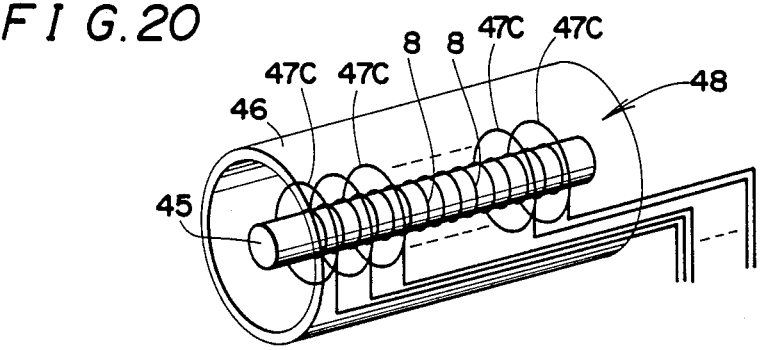

In FIG. 20, a number of independent annular sheathed heaters 47C (1 mm in diameter) charged with carbon powder are aligned inside a furnace core tube 46. A Ni-Ti alloy wire coil 8 wound around a metal mold 45 is inserted inside these sheathed heaters 47C. By passing different currents through individual sheathed heaters 47C (a larger current at the middle region of the wire coil and a smaller current at both ends of the coil), individual regions of the wire coil are annealed at different temperatures as with the coil example (1) to achieve the intended distribution of transition point along the length of coil.

In the case of the coil of example (1), the shape memory alloy coil is endowed with a given distribution of transition point by using different temperature for annealing. It will however be understood from FIG. 15 that the coil can be endowed with such distribution of transition point by annealing individual regions of the coil at a uniform temperature but for different durations of time. For this purpose, in FIG. 19, cooling liquid can be passed through the cooling lines 49 for cooling the coil after a given time during annealing, or in FIG. 20, the independent heaters 47C can be individually switched off at proper timings.

On the other hand, a coil of the example (2) that is annealed to a uniform transition point along the whole length thereof and treated so as to reach the transition point earlier in the middle region thereof than in both end regions thereof for recovery of the original shape at nonuniform timing can be worked as follows. For example, the wire of given end regions of the coil is made thinner so these end regions may have a smaller heat capacity. In the blood vessel, the shape memory alloy coil warms up to a temperature almost equivalent to the body temperature. Coming in contact to a slightly hotter warming water, both end regions of the coil which are made of thinner wire for smaller heat capacity warms as these regions absorb heat energy from the warming water. As a result, the warming water that has been cooled reabsorbs heat energy from the thinner wire regions of the coil to retard heating of such regions.

Figure 21:
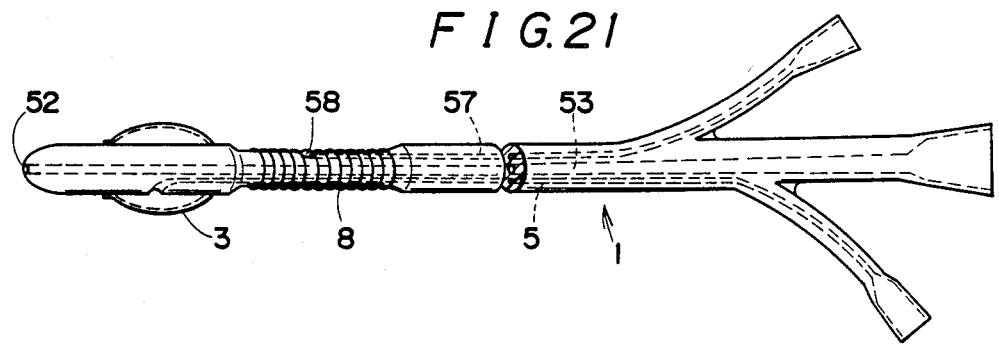
FIG. 21 is a partially omitted front view of still another example of the catheter of the invention.

FIG. 21 is another example of the catheter of the invention.

A catheter 1 of this example, which is made of a silicone rubber, polyurethane elastomer or the like, has an axial lumen 53 that opens at the front end 52 and at the base of catheter, a balloon 3 of elastic rubber that inflates and deflates under pneumatic control with both ends thereof bonded to the outer surface of the top end portion of the catheter, an air lumen 5 with one end thereof opening inside the above balloon and the other end thereof opening at the base of catheter, a tubular coil 8 behind the above balloon made by winding shape memory alloy wire spirally around the outer surface of catheter, and a warming liquid lumen 57 that is made in the catheter and has an outlet port 58 that opens in the outer surface of catheter at a position where the tubular coil is provided, the other end of lumen 57 opening at the base of catheter. It is noted that the outlet port 58 can be made to open below the middle, front or rear regions of the tubular coil.

To use the above catheter for dilation of the stenosis, physiological saline, for example, heated to a constant temperature of 50° C. is injected through the warming liquid lumen 57. Warmed physiological saline thus flows from the outlet port 58 into the blood vessel where the tubular coil is present. The tubular coil is thus heated above the transition point thereof to expand and recover the original shape.

Also in this example, physiological saline, transfusion solution or the like is warmed and used for satisfactory temperature control of shape memory alloy.

Further, when the shape memory alloy coil 8 is uncovered from the sheath 9 to apply to the tissues to be expanded and also when the coil 8 is fully covered with the sheath 9 (or fixed inside the sheath 9), the strain of the coil 8 is preferably in the superelastic region.

Figure 8:
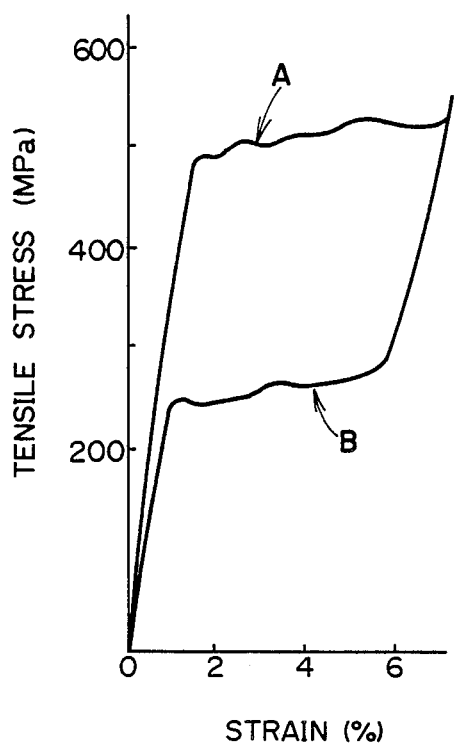
FIG. 8 is a stress-strain diagram of a shape memory alloy.

Namely, the shape memory alloy, for example, Ti-Ni alloy of which the coil 8 is made exhibits the so-called superelasticity effect as shown in FIG. 8 with a hysterisis loop, along the curves A and B of which the stress changes rather little in a wide range of the strain, allowing restoration of the original shape without plastic deformation. Such superelasticity appears when the temperature of the shape memory alloy of which the coil 8 is composed is higher than the Af point. Accordingly, since the coil 8 is designed to be superelastic when inserted to a given position of the patient's organ, the coil 8 as retained in the patient body (at a temperature higher than the Af point) is elastic enough to satisfactorily follow any deformation of the patient's organ, so the coil 8 may exert stable forces to maintain the intended function thereof.

Further, the coil 8 is so designed that when the catheter is inserted with the coil 8 fixed inside the sheath 9, the coil 8 is superelastic. This means that immediately after the insertion into the living body the coil 8 recovers the original shape, so the coil 8 bites the inner surface of sheath 9 to hold itself in position. As a result, there occurs friction between the coil 8 and the sheath 9 and thus the former is hard to go out of the latter. In consideration of such matter, it is preferable to introduce a coolant or cooling liquid to the coil 8 from the inlet 11 of the sheath 9 through the lumen between the catheter body 2 and the sheath 9 so that the coil 8 does not recover the original shape on the insertion of the coil into the living body together with the sheath 9 and catheter body 2. the coolant can be a fluid therapy, a physiological saline solution, a contrast medium and so on. The temperature of the coolant is so selected that it becomes higher by the mixing with a blood and another body liquid at the insertion position of the catheter. The coolant can be continuously introduced until the insertion of the catheter ends or it can be introduced after the insertion, and thereafter the coil 8 is uncoverd from the sheath 9 as shown in FIG. 5 (A) to be gradually heated above the Af point to recover the original shape.

To achieve the above effect, the transformation point Af of coil 8 is preferably below the temperature of patient's organ, for example, body temperature 37° C. and particularly between 10 and 30° C since above the temperature of target organ the coil 8 fails to exhibit the aforementioned superelasticity. In the above desirable range of Af point, the shape memory alloy can properly exert such a characteristic property thereof that the alloy keeps elastic at the working temperature.

In this case, the larger difference between the working temperature ($T_A$) and Af point, $$\Delta T = T_A - Af,$$

the more elastic the alloy is. For this reason, a lower Af point is preferable. Ordinarily, however, the Af point below body temperature is available to use.

In the above example, the Af point is estimated according to the known method from the measurement of the relationship between the electric resistance and temperature.

The above transformation point Af can be controlled arbitrarily by changing the compounding ratio of the major elements Ti and Ni, quantities of additives and heat treatment condition. Additionally the above Ti-Ni alloy is a desirable material because of durability and high compatibility thereof with animal tissues (particularly antithrombic nature thereof) besides the favorable characteristics as mentioned above. The Ti-Ni alloy may contain other elements, for example, Cu, Cr, Zn, Fe, Al, and Mo, but it is preferable that Ni and Ti in total account for 95 weight percent or more of the alloy composition.

It is noted that when the coil 8 is used according to the above example surface of the coil may be coated with teflon or other inactive polymer, an antithrombic polymer such as "cardiothan", or a polymer capable of slowly releasing a drug, such as heparin or urokinase.

It will be evident that various modifications can be made to the described embodiments without departing from the scope of the present invention.

For example, the above shape memory alloy may be variously changed in alloy type, composition and shape. Any alloy type that irreversibly recovers the original shape as in the above examples is applicable. Further, beside the coil shape as mentioned above, a various shape, for example, spiral meshwork can be selected for use. Depending on applications, an alloy type capable of reversible transition (that shrinks when cooled) may also be used. The mounting position and/or working pattern cf the shape memory alloy member need not be limited to the above description. It is noted that the catheter of the invention can be inserted not only in the stenosis of blood vessel but in other locations, for example, such part of blood vessel whose wall has become so thin as to be liable to damages.

As mentioned above, the invention uses warming liquid to warm a shape memory alloy member with which the main body is fitted for expanding, namely, recovery of the original shape. If such expanded shape memory alloy member is retained in the stenosis of blood vessel or the like, the constriction can be safely and satisfactorily dilated while any restenosis can be positively avoided.

What is claimed is:

1. A catheter for insertion of a shape memory alloy endoprosthesis into a stenosis comprising:
   a main body provided with an extensible balloon portion at a leading end thereof;
   a narrow body portion adjacent said balloon portion, fitted therearound with a cylindrical shape memory alloy endoprosthesis;
   a slightly wider body portion at an end of said narrow body portion opposite said balloon portion, forming a bulge portion projecting thereat;
   a first lumen passing through said main body and terminating in said balloon portion for injection fluid into said balloon portion to cause inflation thereof;
   a second lumen passing through said main body to a distal end, through which a guide wire can pass; and
   a sheath substantially covering said main body except for said balloon portion, said sheath forming a third fluid injection lumen defined by an inner surface of said sheath and outer surface of said main body and having an inlet port provided at a rear end thereof to supply a warming fluid to said endoprosthesis located inside a front part of said sheath at said narrow body portion, at a temperature above a transition point of the shape memory alloy, to cause recovery of an original shape of said endoprosthesis.

2. A catheter as claimed in claim 1 wherein strain of said shape memory alloy endoprosthesis is kept in a superelasticity region of said alloy both when fitted to said narrow body portion at the insertion from outside a living body and when inserted into a treatment site of an organ and allow to function.

3. A catheter as recited in claim 1 wherein said endoprosthesis comprises a shape memory alloy metal shaped as a spring sheet coil of a flat cross-section.

4. A catheter as recited in claim 1 wherein said endoprosthesis comprises a shape memory alloy sheet formed to have spaced areas of metal removed therefrom.

5. A catheter as recited in claim 1 wherein said endoprosthesis comprises:
   a shape memory alloy metal, said metal being formed into a cylindrical shape, said metal having been subjected to an annealing process such that when later deformed the metal will be restored to said original preformed cylindrical shape when subjected to a transition temperature, said annealing process including a further treatment such that when said metal is subjected to said transition temperature different areas of said metal will be restored to said original preformed cylindrical shape at different rates.

6. A catheter for insertion of a shape memory alloy endoprosthesis into a stenosis comprising:
   a main body provided with an extensible balloon portion at a leading end thereof;
   a narrow body portion adjacent said balloon portion, fitted therearound with a cylindrical shape memory alloy endoprosthesis;
   a slightly wider body portion at an end of said narrow body portion opposite said balloon portion, forming a bulge portion projecting thereat;
   a first lumen passing through said main body and terminating in said balloon portion for injecting fluid into said balloon portion to cause inflation thereof;
   a second lumen passing through said main body to a distal end, through which a guide wire can pass; and
   a fluid injection means to inject fluid at said narrow body portion to provide irrigation thereat for causing recovering of an original shape of said shape memory alloy endoprosthesis; wherein said shape memory alloy endoprosthesis comprises a shape memory alloy metal, said metal being preformed into a cylindrical shape, said metal having been subjected to an annealing process such that when later deformed the metal will be restored to said original preformed cylindrical shape when subjected to a transition temperature, and a further treatment to cause longitudinal end regions of the endoprosthesis to have a higher transition temperature than a middle region such that when said metal is subjected to said transition temperature said regions of said metal will be restored to said original preformed cylindrical shape at different rates.

7. A catheter for insertion of a shape memory alloy endoprosthesis into a stenosis comprising:
   a main body provided with an extensible balloon portion at a leading end thereof;
   a narrow body portion adjacent said balloon portion, fitted therearound with a cylindrical shape memory alloy endoprosthesis;
   a slightly wider body portion at an end of said narrow body portion opposite said balloon portion, forming a bulge portion projecting thereat;
   a first lumen passing through said main body and terminating in said balloon portion for injecting fluid into said balloon portion to cause inflation thereof;
   a second lumen passing through said main body to a distal end, through which a guide wire can pass; and
   a fluid injection means to inject fluid at said narrow body portion to provide irrigation thereat for causing recovery of an original shape of said shape memory alloy endoprosthesis;
   wherein said shape memory endoprosthesis is a tubular metal sheet such that upon recovery of said original shape the endoprosthesis changes in diameter but not substantially in longitudinal dimension during shape change, said endoprosthesis having a plurality of holes formed in the surface thereof providing openings for contact with tissue.

8. A catheter as claimed in claim 7 wherein said tubular shape memory alloy has a longitudinally continuous portion.

9. A method applying a shape memory metal alloy endoprosthesis to a stenosis comprising the steps of:
   (a) applying a shape memory metal alloy endoprosthesis preformed into cylindrical shape to a narrow body portion of a catheter having a main body portion provided at a leading end thereof with an extensible balloon portion, said endoprosthesis being applied by wrapping said metal about said narrow body portion in a cylindrical form of smaller diameter than said preformed cylindrical shape;
   (b) inserting said catheter into a body passage as far as a stenosis thereof, said balloon portion extending beyond said stenosis;
   (c) inflating said balloon portion to contact an inner wall of said body passage beyond said stenosis so as to stop any flow of body fluid thereon;
   (d) after said balloon portion is inflated, injecting a warming fluid through a lumen in said catheter surrounding the area of said endoprosthesis, said fluid being of temperature such as to restore said endoprosthesis to said original preformed shape to dilate said stenosis;
   (e) deflating said balloon portion of said catheter; and
   (f) removing said catheter, said endoprosthesis remaining in said stenosis.

* * * * *